United States Patent
Kong et al.

(10) Patent No.: US 11,122,856 B2
(45) Date of Patent: Sep. 21, 2021

(54) INTELLIGENT TEMPERATURE CONTROLLER FOR SHOES AND INTELLIGENT TEMPERATURE CONTROLLING SHOE AND INTELLIGENT TEMPERATURE CONTROLLING METHOD THEREOF

(71) Applicants: Deming Kong, Shenzhen (CN); Guanxing Chen, Shenzhen (CN)

(72) Inventors: Deming Kong, Shenzhen (CN); Guanxing Chen, Shenzhen (CN)

( * ) Notice: Subject to any disclaimer, the term of this patent is extended or adjusted under 35 U.S.C. 154(b) by 320 days.

(21) Appl. No.: 15/648,428

(22) Filed: Jul. 12, 2017

(65) Prior Publication Data

US 2018/0064202 A1    Mar. 8, 2018

Related U.S. Application Data

(63) Continuation-in-part of application No. 15/339,848, filed on Oct. 31, 2016, now Pat. No. 11,047,706.

(Continued)

(51) Int. Cl.
  *A43B 7/04*    (2006.01)
  *A43B 7/02*    (2006.01)
  (Continued)

(52) U.S. Cl.
  CPC .............. *A43B 7/04* (2013.01); *A43B 3/001* (2013.01); *A43B 3/0005* (2013.01);
  (Continued)

(58) Field of Classification Search
  None
  See application file for complete search history.

(56) References Cited

U.S. PATENT DOCUMENTS 2,680,918 A * 6/1954 Behner .................... A43B 7/02
                                                        36/2.6
3,360,633 A * 12/1967 Weisberger .......... A43B 3/0005
                                                        219/211

(Continued)

FOREIGN PATENT DOCUMENTS

CN        2473943 Y  *  1/2002
CN        2803267 Y  *  8/2006
(Continued)

OTHER PUBLICATIONS

Machine Translation for CN2803267 (Year: 2006).*
(Continued)

*Primary Examiner* — Catherine T. Rastovski
*Assistant Examiner* — Leonard S Liang
(74) *Attorney, Agent, or Firm* — Raymond Y. Chan; David and Raymond Patent Firm

(57) ABSTRACT

An intelligent temperature controller for shoes includes a master chip, a heating unit, a temperature detecting unit detecting a current temperature of the shoes, a power source and a charging circuit connected with the power source, wherein the master chip is respectively and electrically connected with the heating unit, the temperature detecting unit and the power source, wherein the master chip controls the power source to supply power to the heating unit, wherein the master chip is communicated with an electric device to control the temperature of the shoes and provides operating states feedback to the electric device.

31 Claims, 9 Drawing Sheets

Related U.S. Application Data

(60) Provisional application No. 62/338,513, filed on May 19, 2016.

(51) Int. Cl.

| | |
|---|---|
| *A43B 3/00* | (2006.01) |
| *A43B 17/00* | (2006.01) |
| *G01C 22/00* | (2006.01) |
| *A61F 7/00* | (2006.01) |

(52) U.S. Cl.
CPC .............. *A43B 3/0015* (2013.01); *A43B 7/02* (2013.01); *A43B 17/00* (2013.01); *G01C 22/006* (2013.01); *A61F 2007/0045* (2013.01)

(56) References Cited

U.S. PATENT DOCUMENTS

| | | | | |
|---|---|---|---|---|
| 3,585,736 | A * | 6/1971 | Polichena | A43B 7/02 36/2.6 |
| 3,621,191 | A * | 11/1971 | Cornwell | A41D 19/01535 219/211 |
| 3,761,562 | A * | 9/1973 | Skelham | A43D 11/12 264/346 |
| 4,080,971 | A * | 3/1978 | Leeper | A43B 3/0005 219/211 |
| 4,507,877 | A * | 4/1985 | Vaccari | A43B 3/0005 219/211 |
| 4,665,301 | A * | 5/1987 | Bondy | A43B 7/025 219/211 |
| 4,823,482 | A * | 4/1989 | Lakic | A41D 19/001 165/46 |
| 4,894,931 | A * | 1/1990 | Senee | A43B 3/0005 126/204 |
| 4,910,881 | A * | 3/1990 | Baggio | A43B 3/0005 219/211 |
| 5,041,717 | A * | 8/1991 | Shay, III | A43B 3/0005 219/211 |
| 5,483,759 | A * | 1/1996 | Silverman | A43B 1/0072 36/1 |
| 5,495,682 | A * | 3/1996 | Chen | A43B 3/0005 219/211 |
| 5,565,124 | A * | 10/1996 | Balzano | A43B 7/025 219/528 |
| 5,623,772 | A * | 4/1997 | Sunderland | A43B 3/0031 219/211 |
| 5,956,866 | A * | 9/1999 | Spears | A43B 3/0005 36/136 |
| 6,094,844 | A * | 8/2000 | Potts | A43B 3/0031 36/136 |
| 6,865,825 | B2 * | 3/2005 | Bailey, Sr. | A43B 1/0054 36/29 |
| 8,074,373 | B2 * | 12/2011 | Macher | A43B 3/0005 219/211 |
| 8,869,429 | B1 * | 10/2014 | Zsolcsak | A43B 7/04 36/2.6 |
| 9,101,177 | B2 * | 8/2015 | Whitehead | A43B 3/0015 |
| 9,548,618 | B2 * | 1/2017 | Shapiro | A43B 3/0005 |
| 9,607,652 | B2 * | 3/2017 | Bose | H04N 5/23229 |
| 2002/0133973 | A1 * | 9/2002 | Lin | A43B 7/025 36/2.6 |
| 2005/0028401 | A1 * | 2/2005 | Johnson | A41D 19/01535 36/2.6 |
| 2006/0123660 | A1 * | 6/2006 | Chen | A43B 1/0009 36/2.6 |
| 2007/0039201 | A1 * | 2/2007 | Axinte | A43B 7/025 36/2.6 |
| 2008/0016715 | A1 * | 1/2008 | Vickroy | A43B 7/141 36/2.6 |
| 2008/0197126 | A1 * | 8/2008 | Bourke | A43B 7/025 219/634 |
| 2009/0013554 | A1 * | 1/2009 | Macher | A43B 3/0005 36/2.6 |
| 2009/0193680 | A1 * | 8/2009 | Pang | A43B 3/0005 36/43 |
| 2010/0151996 | A1 * | 6/2010 | Alten | A43B 3/0005 482/8 |
| 2011/0083339 | A1 * | 4/2011 | Luo | A43B 3/0005 36/2.6 |
| 2011/0107771 | A1 * | 5/2011 | Crist | A43B 3/0005 62/3.3 |
| 2011/0296714 | A1 * | 12/2011 | Holzer | A43B 3/0005 36/132 |
| 2012/0005919 | A1 * | 1/2012 | Chen | A43B 7/04 36/2.6 |
| 2012/0018418 | A1 * | 1/2012 | Shantha | A43B 7/02 219/482 |
| 2012/0023785 | A1 * | 2/2012 | Barnes | A43B 7/143 36/141 |
| 2013/0019503 | A1 * | 1/2013 | Vogt | A43B 3/0005 36/103 |
| 2013/0213147 | A1 * | 8/2013 | Rice | G01L 1/20 73/862.046 |
| 2013/0247410 | A1 * | 9/2013 | Tseng | A43B 7/04 36/2.6 |
| 2014/0059894 | A1 * | 3/2014 | Lupinek | A43B 7/34 36/137 |
| 2014/0070957 | A1 * | 3/2014 | Longinotti-Buitoni | G06F 3/011 340/870.01 |
| 2015/0276239 | A1 * | 10/2015 | Fadell | F24D 19/1009 237/2 A |
| 2016/0165965 | A1 * | 6/2016 | Ellis | A43B 3/0005 434/81 |
| 2017/0142501 | A1 * | 5/2017 | Jakobsson | H04Q 9/00 |
| 2017/0232300 | A1 * | 8/2017 | Tran | G16H 20/30 434/247 |
| 2017/0238870 | A1 * | 8/2017 | Lee | A43B 3/0005 |
| 2017/0299199 | A1 * | 10/2017 | Daniels | F24D 19/10 |
| 2018/0028861 | A1 * | 2/2018 | Murakoshi | A61B 5/6829 |

FOREIGN PATENT DOCUMENTS

| | | | | |
|---|---|---|---|---|
| CN | 2829414 | Y * | 10/2006 | |
| CN | 201234602 | Y * | 5/2009 | ............ A43B 3/001 |
| CN | 201238666 | Y * | 5/2009 | |
| CN | 201683126 | U * | 12/2010 | ............ A43B 3/001 |
| CN | 201700499 | U * | 1/2011 | |
| CN | 102028328 | A * | 4/2011 | |
| CN | 201878895 | U * | 6/2011 | |
| CN | 201995701 | U * | 10/2011 | |
| CN | 202035536 | U * | 11/2011 | |
| CN | 102266144 | A * | 12/2011 | |
| CN | 202151145 | U * | 2/2012 | ............ A43B 3/001 |
| CN | 102589257 | A * | 7/2012 | |
| CN | 202396563 | U * | 8/2012 | |
| CN | 202635782 | U * | 1/2013 | |
| CN | 102960897 | A * | 3/2013 | |
| CN | 203105805 | U * | 8/2013 | |
| CN | 103720115 | A * | 4/2014 | |
| CN | 203618875 | U * | 6/2014 | |
| CN | 203692655 | U * | 7/2014 | |
| CN | 203913586 | U * | 11/2014 | |
| CN | 104207409 | A * | 12/2014 | |
| CN | 104287277 | A * | 1/2015 | |
| CN | 204091051 | U * | 1/2015 | |
| CN | 204091135 | U * | 1/2015 | |
| CN | 104464189 | A * | 3/2015 | |
| CN | 104522932 | A * | 4/2015 | ............ A43B 7/02 |
| CN | 104544714 | A * | 4/2015 | |
| CN | 104544715 | A * | 4/2015 | |
| CN | 104605571 | A * | 5/2015 | |
| CN | 104687636 | A * | 6/2015 | |
| CN | 204409759 | U * | 6/2015 | |
| CN | 105192995 | A * | 12/2015 | |
| CN | 204838206 | U * | 12/2015 | |
| CN | 105212424 | A * | 1/2016 | |
| CN | 105342617 | A * | 2/2016 | |
| CN | 205251543 | U * | 5/2016 | |
| CN | 105815874 | A * | 8/2016 | |

(56) References Cited

FOREIGN PATENT DOCUMENTS

| CN | 205432341 U | * | 8/2016 | ............ A43B 7/04 |
| CN | 205585412 U | * | 9/2016 | |
| CN | 107242638 A | * | 10/2017 | |
| WO | WO-2016086491 A1 | * | 6/2016 | ............ A43B 7/02 |

OTHER PUBLICATIONS

Machine Translation for CN2829414 (Year: 2006).*
Machine Translation for CN 102028328 (Year: 2011).*
Machine Translation for CN 102266144 (Year: 2011).*
Machine Translation for CN 102589257 (Year: 2012).*
Machine Translation for CN 102960897 (Year: 2013).*
Machine Translation for CN 103720115 (Year: 2014).*
Machine Translation for CN 104207409 (Year: 2014).*
Machine Translation for CN 104287277 (Year: 2015).*
Machine Translation for CN 104464189 (Year: 2015).*
Machine Translation for CN 104522932 (Year: 2015).*
Machine Translation for CN 104544714 (Year: 2015).*
Machine Translation for CN 104544715 (Year: 2015).*
Machine Translation for CN 104605571 (Year: 2015).*
Machine Translation for CN 104687636 (Year: 2015).*
Machine Translation for CN 105192995 (Year: 2015).*
Machine Translation for CN 105212424 (Year: 2016).*
Machine Translation for CN 105342617 (Year: 2016).*
Machine Translation for CN 105815874 (Year: 2016).*
Machine Translation for CN 107242638 (Year: 2017).*
Machine Translation for CN201234602 (Year: 2009).*
Machine Translation for CN201238666 (Year: 2009).*
Machine Translation for CN201683126 (Year: 2010).*
Machine Translation for CN201700499 (Year: 2011).*
Machine Translation for CN201878895 (Year: 2011).*
Machine Translation for CN201995701 (Year: 2011).*
Machine Translation for CN202035536 (Year: 2011).*
Machine Translation for CN202151145 (Year: 2012).*
Machine Translation for CN202396563 (Year: 2012).*
Machine Translation for CN202635782 (Year: 2013).*
Machine Translation for CN203105805 (Year: 2013).*
Machine Translation for CN203618875 (Year: 2014).*
Machine Translation for CN203692655 (Year: 2014).*
Machine Translation for CN203913586 (Year: 2014).*
Machine Translation for CN204091051 (Year: 2015).*
Machine Translation for CN204091135 (Year: 2015).*
Machine Translation for CN204409759 (Year: 2015).*
Machine Translation for CN204838206 (Year: 2015).*
Machine Translation for CN205251543 (Year: 2016).*
Machine Translation for CN205432341 (Year: 2016).*
Machine Translation for CN205585412 (Year: 2016).*
Machine Translation for WO2016086491 (Year: 2016).*
Steve Holt; "ThermaCELL heated insoles review"; https://the-gadgeteer.com/2015/05/19/thermacell-heated-insoles-review/; May 19, 2015. (Year: 2015).*
"App controls heat, comfort, fitness monitors in smart shoe"; https://applysci.com/app-controls-heat-comfort-fitness-monitors-in-smart-shoe/; Jan. 5, 2016. (Year: 2016).*
Ben Coxworth; "App-controlled insoles bring the heat"; https://newatlas.com/pluswinter-heated-insoles/46879/; Dec. 9, 2016. (Year: 2016).*
Amanda Kooser; "Heated smart insoles keep your tootsies toasty"; https://www.cnet.com/news/heated-smart-insoles-keep-your-tootsies-toasty/; Sep. 2, 2014. (Year: 2014).*
UGALE—The First Insole With Active Ventilating System; Kickstarter Campaign; https://www.kickstarter.com/projects/vaytechnologies/ugale-the-first-insole-with-active-ventilating-sys; Last updated Jul. 17, 2015. (Year: 2015).*
"Digitsole: The first interactive insole to heat your feet"; Kickstarter Campaign; https://www.kickstarter.com/projects/1308642275/digitsole-the-first-interactive-insole-to-heat-you; p. 20 indicates that the Funding period was from Sep. 2, 2014-Nov. 1, 2014. (Year: 2014).*
Abstract and Figure for Feng et al (CN201422482Y) (Year: 2010).*
Rick Broida; "Smart insole promises to stop stinky feed"; https://www.cnet.com/news/smart-insole-promises-to-stop-stinky-feet/; Jun. 4, 2015 (Year: 2015).*

* cited by examiner

INTELLIGENT TEMPERATURE CONTROLLER FOR SHOES AND INTELLIGENT TEMPERATURE CONTROLLING SHOE AND INTELLIGENT TEMPERATURE CONTROLLING METHOD THEREOF

CROSS REFERENCE OF RELATED APPLICATION

This is a Continuation-In-Part application that claims the benefit of priority under 35U.S.C. § 120 to a non-provisional application, application Ser. No. 15/339,848, filed Oct. 31, 2016, which is a non-provisional application that claims the benefit of priority under 35U.S.C. § 120 to a provisional application, application No. 62/388,513, filed May 19, 2016, and priority under 35U.S.C. § 119 to a Chinese invention application, application number CN 201610082327.7, filed on Feb. 5, 2016, the entire contents of each of which are expressly incorporated herewith by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an intelligent temperature controller, and more particularly to an intelligent temperature controller for shoes and intelligent temperature controlling shoes and intelligent temperature controlling method thereof.

Description of Related Arts

The foot brings together the reflex zones of the human body, which is known as the "second heart". As a result, protecting the foot and preventing the foot from frostbite are essential. An electric shoe heating the foot is one of the protective devices. The electric shoe generally has a heating element which can be an ordinary metal resistance wire or a conductive carbon fiber. However, the electric shoes with the ordinary metal resistance wire are cumbersome and are inconvenient; the metal resistance wire is easy to break.

A disadvantage of the traditional electric shoes in the market is the weakness on controlling the temperature. The traditional electric shoes are turned off or turned on by hands, when the temperature is too high, users have to turn off by hands; when the temperature is too low, and users also have to turn off by hands. In a word, the temperature of the traditional electric shoes cannot be automatically controlled, and thus it is inconvenient for users to use, especially for the aged people.

Another disadvantage of the traditional electric shoes in the market is weakness on comfort level. The traditional electric shoes include a rechargeable battery and the rechargeable battery is installed near the soles of the heel and is easy to be deformed. In addition, the shell of the rechargeable battery is designed to increase the thickness or the stiffness in order to withstand heavy loads. As a result, the entire traditional electric shoes are heavy and users wearing the electric shoes have a low comfort level.

Another disadvantage of the traditional electric shoes in the market is that the main body of the traditional electric shoes and the temperature controlling member are not easy to assemble and disassemble, the higher the cost of production and maintenance;

Another disadvantage of the traditional electric shoes in the market is weakness on maintaining the temperature inside of the shoes in a preset range.

SUMMARY OF THE PRESENT INVENTION

The invention is advantageous in that it provides an intelligent temperature controller for shoes and intelligent temperature controlling shoes and intelligent temperature controlling method thereof, which can adaptively and automatically adjust the temperature inside the shoes.

Another advantage of the invention is to provide an intelligent temperature controller for shoes and intelligent temperature controlling shoes and intelligent temperature controlling method thereof, which is controlled by wireless communications.

Another advantage of the invention is to provide an intelligent temperature controller for shoes and intelligent temperature controlling shoes and intelligent temperature controlling method thereof, which has a quick charging performance.

Another advantage of the invention is to provide an intelligent temperature controller for shoes and intelligent temperature controlling shoes and intelligent temperature controlling method thereof, which has a small and sample size and is portable to be installed.

Another advantage of the invention is to provide an intelligent temperature controller for shoes and intelligent temperature controlling shoes and intelligent temperature controlling method thereof, wherein the intelligent temperature controller is adapted for being installed in various types of shoes.

Another advantage of the invention is to provide an intelligent temperature controller for shoes and intelligent temperature controlling shoes and intelligent temperature controlling method thereof, which controls the temperature inside of the shoes rapidly and reduces the loss energy.

Another advantage of the invention is to provide an intelligent temperature controller for shoes and intelligent temperature controlling shoes and intelligent temperature controlling method thereof, which maintains the current temperature within a predetermined range.

Another advantage of the invention is to provide an intelligent temperature controller for shoes and intelligent temperature controlling shoes and intelligent temperature controlling method thereof, which has a pulse current generation unit of the intelligent temperature controller for shoes providing a pulse current to the heating unit.

Additional advantages and features of the invention will become apparent from the description which follows, and may be realized by means of the instrumentalities and combinations particular point out in the appended claims.

According to the present invention, the foregoing and other objects and advantages are attained by an intelligent temperature controller for shoes, comprising:

a master chip, a heating unit, a temperature detecting unit which detects a current temperature of the shoes, a power source and a charging circuit connected with the power source, wherein the master chip is respectively and electrically connected with the heating unit, the temperature detecting unit and the power source, wherein the master chip controls the power source to supply power to the heating unit, wherein the master chip is communicated with an electric device to control the temperature of the shoes and provides operating states feedback to the electric device.

According to the present invention, the foregoing and other objects and advantages are also attained by an intelligent temperature controlling shoe, comprising:

an intelligent temperature controller and a shoe body, wherein the intelligent temperature controller is installed in the shoe body and control the temperature of the inside of the shoe body, wherein the intelligent temperature controller comprises:

a master chip, a heating unit, a temperature detecting unit detected a current temperature of the shoes, a power source and a charging circuit connected with the power source, wherein the master chip is respectively and electrically connected with the heating unit, the temperature detecting unit and the power source, wherein the master chip controls the power source to supply power to the heating unit, wherein the master chip is communicated with an electric device to control the temperature of the shoes and provides operating states feedback to the electric device.

According to the present invention, the foregoing and other objects and advantages are also attained by an intelligent temperature controlling method for shoes, comprising the steps of:

pairing and communicating an intelligent temperature controller for shoes with an electric device;

receiving a temperature control signal from the electric device by the intelligent temperature controller;

supplying power to a heating unit of the intelligent temperature controller;

detecting a current temperature of the shoes; and maintaining the current temperature within a predetermined range.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
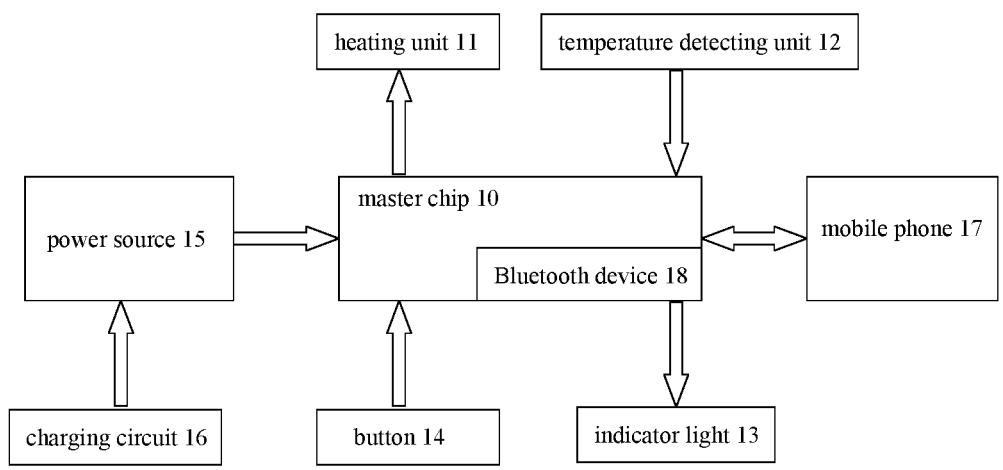
FIG. 1 is a diagram of an intelligent temperature controller for shoes according to a preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIG. 1, FIG. 4, FIG. 5, FIG. 6 and FIG. 7 of the drawings, an intelligent temperature controller for shoes according to a preferred embodiment of the present invention is illustrated, wherein the intelligent temperature controller for shoes comprises a master chip 10, a heating unit 11, a temperature detecting unit 12, an indicator light 13, a button 14, a power source 15 and a charging circuit 16. The indicator light 13 is implemented as a light-emitting diode and the charging circuit 16 is implemented as a quick-acting charging circuit.

The master chip 10 is respectively and electrically connected with the heating unit 11, the temperature detecting unit 12, the indicator light 13, the button 14 and the power source 15. The power source 15 is electrically connected with the charging circuit 16. The users are able to control the operating state of the heating unit 11 via the button 14.

The master chip 10, the heating unit 11 and the temperature detecting unit 12 are electrically connected to automatically control the temperature of the inside of the shoes. The temperature detecting unit 12 detects the temperature of the inside of the shoes and converts the detected temperature data into electrical signal, then the temperature detecting unit 12 transmits the converted electrical signal relating to the detected temperature data to the master chip 10. The master chip 10 controls the operative mode of the heating unit 11 according to the transmitted electrical signal relating to the detected temperature data.

Preferably, the heating unit 11 is implemented as a heating unit with high power and high conversion efficiency, and the power source 15 is implemented as polymer Li-ion battery, so that the circuit with the master chip 10, the heating unit 11 and the temperature detecting unit 12 has a sample structure and is efficient. Moreover, as the heating unit 11 is implemented as a heating unit with high power and high conversion efficiency, the temperature is rapidly increased. In addition, as the power source 15 is implemented as polymer Li-ion battery and has a small size, the entire size of the intelligent temperature controller for shoes is reduced, thereby reducing the loss in energy. The intelligent temperature controller of the present invention is adapted for being mounted inside of the shoes. Preferably, the charging circuit 16 has a USB interface for charging the power source 15 quickly. In an embodiment, the intelligent temperature controller can be charged up to 100% in two to three hours, thereby enhancing the user experience. In other embodiment, the charging circuit 16 also has a charge controlling part to control the charging process and automatically turn-off ceases to be charged.

It is worth mentioning that the intelligent temperature controller for shoes of the present invention not only automatically controls the temperature inside of the shoes and feeds back operating status to users, but also adjusts the operating status in response to users' requests. The intelligent temperature controller for shoes of the present invention is able to communicate with users by many modern wireless communication technologies such as Bluetooth transmission technology and Internet transmission technology.

It is worth mentioning that the heating unit 11 can be implemented as far infrared carbon fiber wire having remote infrared carbon fiber heating layers, and when the heating unit 11 is supplied with power, the heating unit 11 generates a wavelength of 7-12 μm far infrared wave, so that various parts of the foot are stimulated and the health effects are improved.

More specifically, as shown in FIG. 1 of the drawings, the intelligent temperature controller for shoes of the present invention communicated with users by Bluetooth transmission technology is illustrated. The master chip 10 is provided with a Bluetooth device 18 based on Bluetooth Low Energy Wireless Technology. The Bluetooth device 18 is communicated with a portable electronic device such as a mobile phone 17. The mobile phone 17 is installed with software providing an interactive interface for users and the intelligent temperature controller for shoes of the present invention. In other words, the intelligent temperature controller is able to feed back the temperature information to users and able to adjust the temperature and other operative states in response to the users' actions on the interactive interface of the software of the mobile phone 17. One skilled in the art will understand that the mobile phone 17 is exemplary only and not intended to be limiting, in other embodiment, the interactive interface is provided by other platforms of electronic devices such as software of computers. In other words, users can have interactions with the intelligent temperature controller for shoes of the present invention using interactive interface of the software of the electronic devices conveniently.

More specifically, based on the Bluetooth Low Energy Wireless Technology, as the mobile phone 17 is internally installed with Bluetooth adapter, the temperature and other data information can directly transmitted from the intelligent temperature controller for shoes of the present invention to the mobile phone 17. Moreover, according to the Session Initiation Protocol (SIG), each Bluetooth device has a unique MAC address to uniquely identify the Bluetooth device. This MAC address is obtained by the authentication of Bluetooth Qualification Body. In the preferred embodiment, the Bluetooth device 18 has a Bluetooth chip with a unique MAC address to uniquely identify. Preferably, the Bluetooth device 18 of the intelligent temperature controller for shoes is paired with the mobile phone 17 by scanning unique QR codes with unique MAC address of the Bluetooth device 18. In other words, the QR codes with unique MAC address of the Bluetooth device 18 is implemented as images printed on surface of the intelligent temperature controller for shoes, the mobile phone 17 acquires the unique MAC address from the Bluetooth device 18 and pairs with the Bluetooth device 18. One skilled in the art will understand that the above QR codes scanning identification is exemplary only and the Bluetooth device 18 of the intelligent temperature controller for shoes can be identified using other methods.

It is worth mentioning that after the first Bluetooth pairing, the Bluetooth device 18 of the intelligent temperature controller for shoes can automatically pair with the mobile phone 17, thereby users having interactions with the intelligent temperature controller for shoes of the present invention using interactive interface of the software of the electronic devices conveniently.

More specifically, after the Bluetooth device 18 of the intelligent temperature controller for shoes is paired with the mobile phone 17, the time information and the heating temperature of the intelligent temperature controller for shoes can be controlled in response to users' requests transmitted from the interactive interface of the software of the mobile phone 17. Moreover, the operation status of the intelligent temperature controller for shoes also can feed back to users through the interactive interface of the software of the mobile phone 17.

Figure 13:
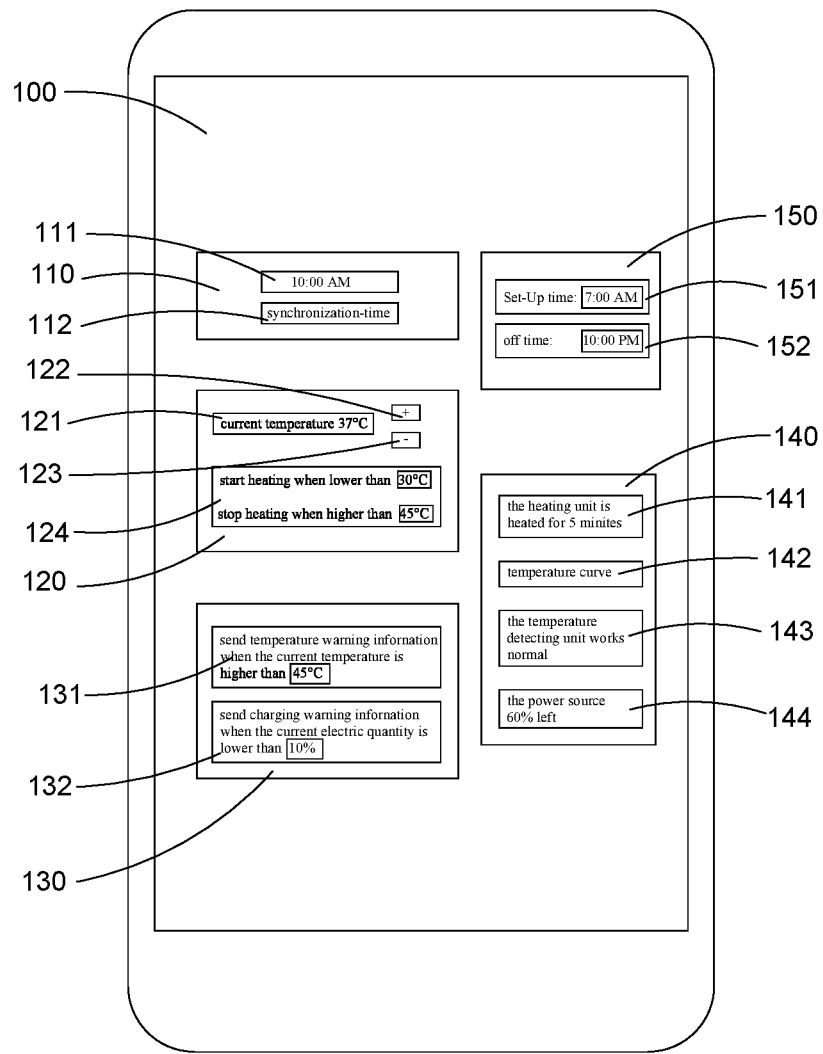
FIG. 13 is a diagram of an intelligent temperature controller for shoes according to the preferred embodiment of the present invention, illustrating am interactive interface of software of an electric device.

As shown in FIG. 13 of the drawings, an interactive interface 100 of the software of the mobile phone 17 is illustrated as an example. The interactive interface 100 comprises a time page section 110, a temperature controlling page section 120, a warning page section 130, an operating state feedback page section 140 and an appointment page section 150.

Specifically, the time page section 110 indicates time setting and display of the intelligent temperature controller for shoes. The time page section 110 comprises a sub section 111 and a sub section 112. The current time information of the intelligent temperature controller is transmitted by the master chip 10 to the mobile phone 17 and is displayed on the sub section 111. If users want to synchronize the current time of the mobile phone 17 with the current time of the intelligent temperature controller as the current time of the mobile phone 17 is synchronized with the international standard time through, he or she sends a request by selecting the sub section 112, in response to the user's request, the mobile phone 17 sends the current international standard time to the master chip 10 of the intelligent temperature controller for modification, so that the synchronized current time information of the intelligent temperature controller is again transmitted by the master chip 10 to the mobile phone 17 and is displayed on the sub section 111. One skilled in the art will understand that the time page section 110 also has other sub sections and described above is exemplary only and not intended to be limiting.

Specifically, the temperature controlling page section 120 indicates the current temperature of the intelligent temperature controller for shoes and provides temperature controlling to users. The temperature controlling page section 120 comprises a sub section 121, a sub section 122, a sub section 123 and a sub section 124. The current temperature data of the shoes is acquired by the temperature detecting unit 12 and is transmitted by the master chip 10 to the mobile phone 17, and the current temperature information is displayed on the sub section 121 of the temperature controlling page section 120. In response to a selecting action of users indicating a temperature rising request on the sub section 122, the master chip 10 receives the temperature rising request and the heating unit 11 starts heating to the users' desired temperature. For example, if user's desired temperature is 37° C., when the current temperature is close to 37° C., the master chip 10 controls the heating unit 11 to reduce the output power until the current temperature is 37° C. In response to a selecting action of users indicating a temperature reducing request on the sub section 123, the master chip 10 receives the temperature reducing request and the temperature detecting unit 12 detects the current temperature of the shoes. According to the current temperature of the shoes, the master chip 10 controls the heating unit 11 starts heating to the users' desired temperature or directly stops heating. In response to a selecting action of users indicating a temperature range controlling request on the sub section 124, the master chip 10 acquires the temperature range such as 30° C. to 45° C. According the acquired temperature range, the master chip 10 acquires the current temperature of the shoes detected by the temperature detecting unit 12 and controls the heating unit 11 to start heating or to stop heating when the detected current temperature of the shoes is out of the temperature range, so that the current temperature of the shoes is controlled within the required temperature range of users and the intelligent temperature controller is capable of automatically controlling the temperature range of the shoes. One skilled in the art will understand that temperature range such as 30° C. to 45° C. is adjusted by users via the sub section 124 of the interactive interface 100 of the software of the mobile phone 17. One skilled in the art will understand that the temperature controlling page section 120 also has other sub sections and described above is exemplary only and not intended to be limiting.

Specifically, the operating state feedback page section 140 indicates the operating states of the members of the intelligent temperature controller. For example, The operating state feedback page section 140 comprises a sub section 141, a sub section 142, a sub section 143, and a sub section 144. The master chip 10 monitors the operating state of the heating unit 11, the temperature detecting unit 12, the power source 15 and the charging circuit 16 and transmits the operating states to the mobile phone 17, and the operating states are displayed on the operating state feedback page section 140 of the interactive interface 100. The sub section 141 of the operating state feedback page section 140 indicates the operating state of the heating unit 11; the sub section 142 of the operating state feedback page section 140 indicates a temperature curve detected by the temperature detecting unit 12; the sub section 143 of the operating state feedback page section 140 indicates the operating state of the temperature detecting unit 12; the sub section 144 of the operating state feedback page section 140 indicates the operating state of the power source 15. One skilled in the art will understand that the operating state feedback page section 140 also has other sub sections to display the feedback operating information of the intelligent temperature controller, so that users are able to clearly obtain the operating states of the intelligent temperature controller for shoes.

Specifically, the warning page section 130 indicates warning information of the intelligent temperature controller. For example, the warning page section 130 comprises a sub section 131 and a sub section 132. In response to a temperature set of users indicating a temperature warning request on the sub section 131, the master chip 10 acquires the current temperature detected by the temperature detecting unit 12, when the acquired current temperature is higher than the set temperature of users such as 45° C., the master chip 10 sends temperature warning information to the mobile phone 17, and the temperature warning information is displayed on the sub section 131 of the warning page section 130, so that users are able to obtain the temperature warning information and to take measure to keep safety, especially when the shoes with the intelligent temperature controller are worn by kids and aged people. As guardians for the kids and the aged people, the intelligent temperature controller for shoes provides a long-range controlling function, thereby guardians taking care of the kids and aged people. In response to an electric quantity set of users indicating a charging warning request on the sub section 132, the master chip 10 acquires the current electric quantity of the power source 15, when the acquired current electric quantity of the power source 15 is less than the set electric quantity of users such as 10%, the master chip 10 sends charging warning information to the mobile phone 17, and the charging warning information is displayed on the sub section 132 of the warning page section 130, so that users are able to obtain the charging warning information and to charge the intelligent temperature controller in time. One skilled in the art will understand that warning temperature such as 45° C. and the set electric quantity such as 10% are adjusted by users respectively via the sub sections 131 and 132 of the interactive interface 100 of the software of the mobile phone 17. One skilled in the art will understand that the warning page section 130 also has other sub sections and described above is exemplary only and not intended to be limiting.

Specifically, the appointment page section 150 indicates appointment time of automatically turning on and off of the intelligent temperature controller. The appointment page section 150 comprises a sub section 151 and a sub section 152. In response to a turning on set of users indicating a set-up request in a predetermined time such as 7:00 AM on the sub section 151, the master chip 10 acquires the current time information, and when the current time is the predetermined 7:00 AM, the master chip 10 controls the heating unit 11 to start heating. For example, if users needs to go outside with shoes in 7:20 AM, the shoes is heated by the intelligent temperature controller in advance, thereby users going outside wearing warm heated shoes. In response to a turning of set of users indicating an off request in a predetermined time such as 10:00 PM on the sub section 152, the master chip 10 acquires the current time information, and when the current time is the predetermined 10:00 PM, the master chip 10 performs turning off of the entire intelligent temperature controller. For example, if user is back home in 9:30 PM; although he or she already takes off the shoes, the shoes can be drying in 30 minutes and the intelligent temperature controller automatically stop working in 10:00 PM. One skilled in the art will understand that the appointment page section 150 also has other sub sections and described above is exemplary only and not intended to be limiting.

One skilled in the art will understand that the interactive interface 100 also has other page sections and described above is exemplary only and not intended to be limiting.

Figure 7:
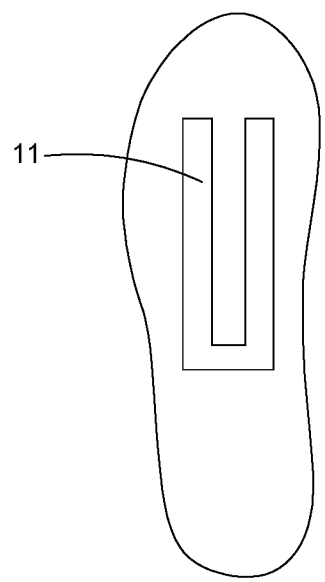
FIG. 7 is a perspective view of the intelligent temperature controller for shoes according to the preferred embodiment of the present invention.

As shown in FIG. 7 of the drawings, the size and shape of the heating unit 11 is adjustable according to different requirements when the intelligent temperature controller is installed on the bottom of the shoes.

In addition, although the Bluetooth Low Energy Wireless Technology is convenient to operate and is faster to communicate, the Bluetooth Technology has a distance limitation; as a result, the intelligent temperature controller for shoes also provides a network wireless transmission to enhance the communication distance with the users.

Figure 3:
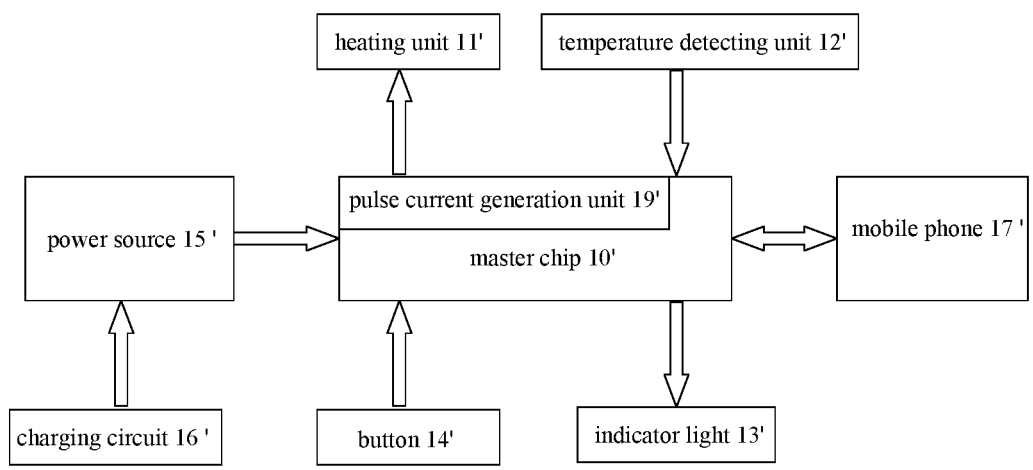
FIG. 3 is a diagram of an intelligent temperature controller for shoes according to an alternative mode of the preferred embodiment of the present invention.
Figure 4:
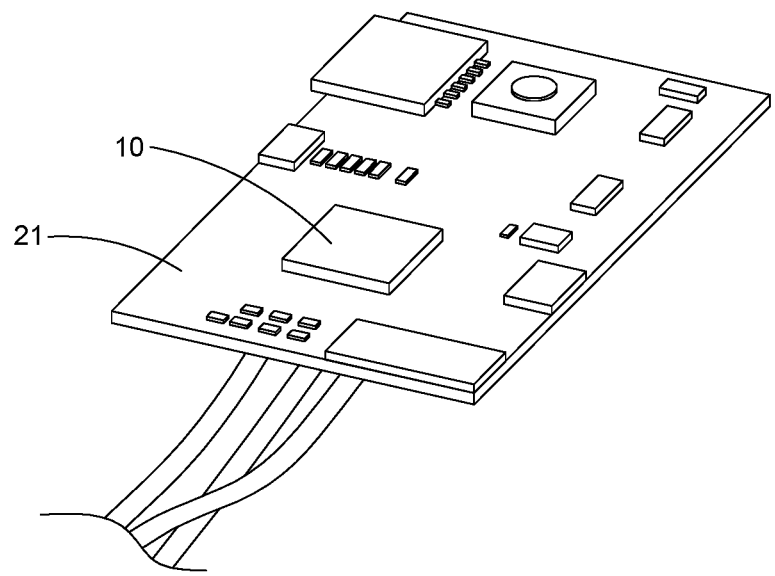
FIG. 4 is a perspective view of the intelligent temperature controller for shoes according to the preferred embodiment of the present invention.
Figure 5:
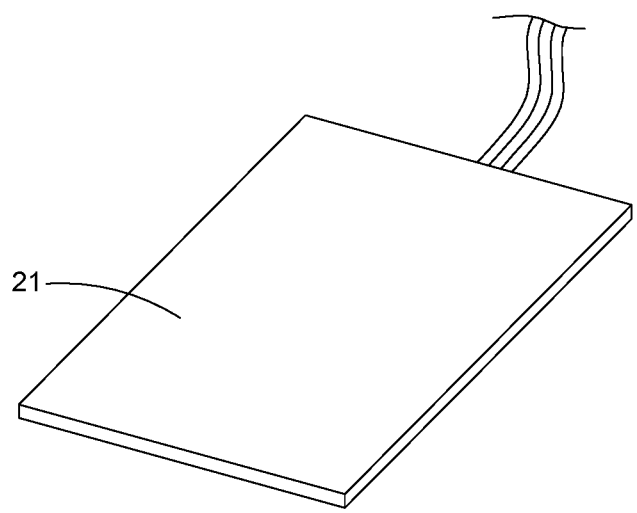
FIG. 5 is a perspective view of the intelligent temperature controller for shoes according to the preferred embodiment of the present invention.
Figure 6:
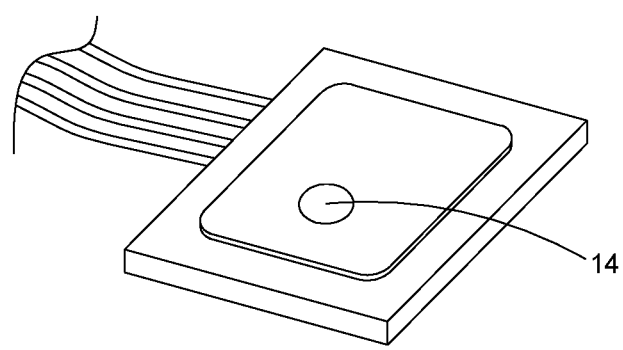
FIG. 6 is a perspective view of the intelligent temperature controller for shoes according to the preferred embodiment of the present invention.

Referring to FIG. 3 of the drawings, the intelligent temperature controller for shoes according to an alternative mode of the preferred embodiment is illustrated, wherein the intelligent temperature controller for shoes comprises a master chip 10', a heating unit 11', a temperature detecting unit 12', an indicator light 13', a button 14', a power source 15' and a charging circuit 16'. The master chip 10' is respectively and electrically connected with the heating unit 11', the temperature detecting unit 12', the indicator light 13', the button 14' and the power source 15'. The power source 15' is electrically connected with the charging circuit 16'. The master chip 10', the heating unit 11' and the temperature detecting unit 12' are electrically connected to automatically control the temperature of the inside of the shoes. The temperature detecting unit 12' detects the temperature of the inside of the shoes and converts the detected temperature data into electrical signal, then the temperature detecting unit 12' transmits the converted electrical signal relating to the detected temperature data to the master chip 10'. The master chip 10 controls the operative mode of the heating unit 11' according to the transmitted electrical signal relating to the detected temperature data. The master chip 10' is communicated with a mobile phone 17'.

Compared with the intelligent temperature controller for shoes of the preferred embodiment, the intelligent temperature controller for shoes of the alternative mode as shown in FIG. 3 of the drawings has a similar structure with the intelligent temperature controller for shoes of the preferred embodiment. The difference is that the intelligent temperature controller for shoes of the alternative mode further comprises a pulse current generation unit 19' connected to the master chip 10'. The pulse current generation unit 19' provides a continuous pulse supply. When the temperature of the intelligent temperature controller for shoes is reached to a user's predetermined value, the pulse current generation unit 19' generates pulse current and the intelligent temperature controller for shoes is powered by the pulse current generation unit 19' instead of the power source 15' so as to maintain the temperature in the predetermined value, thereby saving electricity.

It is worth mentioning that the intelligent temperature controller for shoes of the alternative mode as shown in FIG. 3 of the drawings is able to communicate with the mobile phone 17' via the Bluetooth Low Energy Wireless Technology like the preferred embodiment thereof, the intelligent temperature controller for shoes of the alternative mode also is able to communicate with the mobile phone 17' via the Internet.

Figure 14:
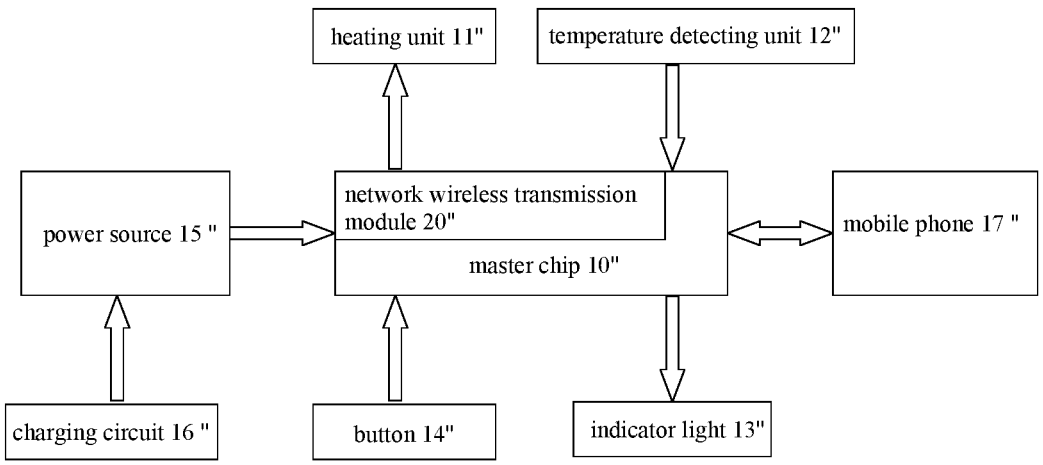
FIG. 14 is a diagram of an intelligent temperature controller for shoes according to an alternative mode of the preferred embodiment of the present invention.

Referring to FIG. 14 of the drawings, the intelligent temperature controller for shoes according to an alternative mode of the preferred embodiment is illustrated, wherein the intelligent temperature controller for shoes comprises a master chip 10", a heating unit 11", a temperature detecting unit 12", an indicator light 13", a button 14", a power source 15" and a charging circuit 16". The master chip 10" is respectively and electrically connected with the heating unit 11", the temperature detecting unit 12", the indicator light 13", the button 14" and the power source 15". The power source 15" is electrically connected with the charging circuit 16". The master chip 10", the heating unit 11" and the temperature detecting unit 12" are electrically connected to automatically control the temperature of the inside of the shoes. The temperature detecting unit 12" detects the temperature of the inside of the shoes and converts the detected temperature data into electrical signal, then the temperature detecting unit 12" transmits the converted electrical signal relating to the detected temperature data to the master chip 10". The master chip 10 controls the operative mode of the heating unit 11" according to the transmitted electrical signal relating to the detected temperature data. The master chip 10" is communicated with a mobile phone 17".

In other words, the intelligent temperature controller for shoes of the alternative mode has similar structure with the intelligent temperature controller for shoes of the preferred embodiment; the difference is the data transfer mode. The intelligent temperature controller for shoes of the preferred embodiment is communicated with the mobile phone 17 via the Bluetooth Low Energy Wireless Technology. The intelligent temperature controller for shoes of the alternative mode is communicated with the mobile phone 17" via the wireless transmission network. Specifically, the intelligent temperature controller for shoes further comprises a network wireless transmission module 20" connected with the master chip 10". The data information from the master chip 10" of the intelligent temperature controller for shoes is transmitted by the network wireless transmission module 20" to the mobile phone 17" via the Internet.

It is worth mentioning that the data information from the master chip 10" of the intelligent temperature controller for shoes is able to be transmitted by the network wireless transmission module 20" and stored under Cloud Computing Services in real time. Users are able to obtain the data information from the master chip 10" of the intelligent temperature controller for shoes from the Cloud Computing Services via the Internet after authentication and identification.

Referring to FIG. 8 to FIG. 12 of the drawings, an intelligent temperature controlling shoe according to an embodiment of the present invention is illustrated, wherein the intelligent temperature controlling shoe comprises a shoe sole 210 and a shoe upper 220 provided on the upper of the shoe sole 210. The intelligent temperature controlling shoe further comprises an intelligent temperature controller 1000. The structure of the intelligent temperature controller 1000 are able to be implemented as the above mentioned intelligent temperature controller for shoes.

Figure 8:
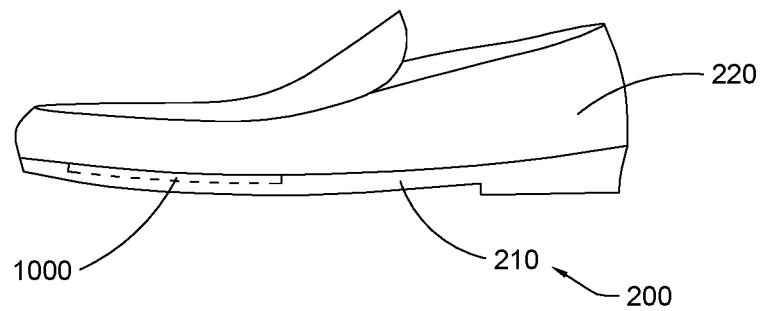
FIG. 8 is a perspective view of an intelligent temperature controlling shoe according to an embodiment of the present invention.
Figure 9:
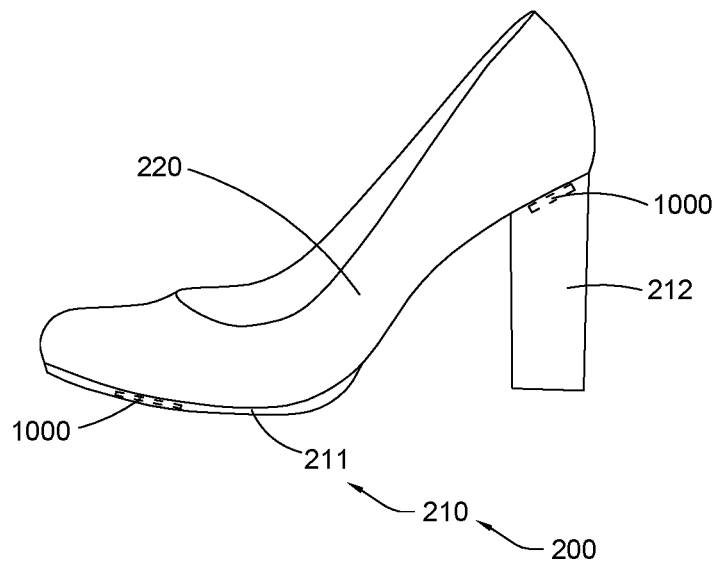
FIG. 9 is a perspective view of the intelligent temperature controlling shoe according to the embodiment of the present invention.
Figure 10:
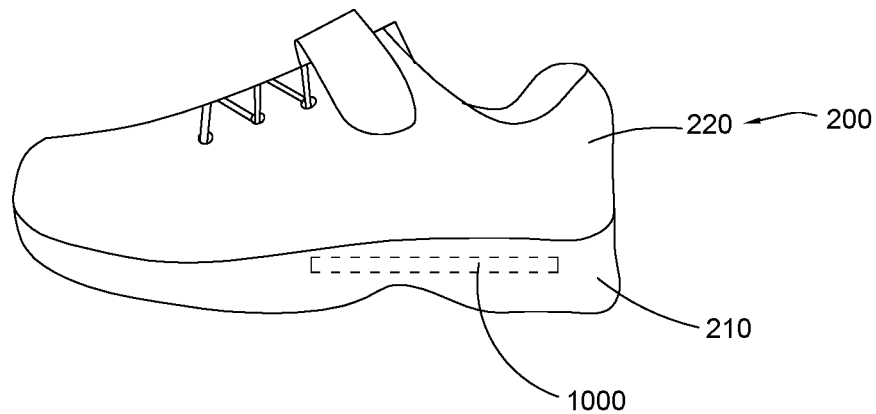
FIG. 10 is a perspective view of the intelligent temperature controlling shoe according to the embodiment of the present invention.

The intelligent temperature controller 1000 is adapted to be installed in many positions of the intelligent temperature controlling shoe. As shown in FIG. 8 of the drawings, the intelligent temperature controlling shoe 200 is implemented as a leather shoe. The intelligent temperature controller 1000 is installed in the shoe sole 210. As shown in FIG. 9 of the drawings, the intelligent temperature controlling shoe 200 is implemented as a high-heeled shoe. The intelligent temperature controlling shoe 200 comprises two intelligent temperature controllers 1000 respectively installed in a front sole 211 of the shoe sole 210 and in a rear sole 212 of the sole 210. The installed position of the intelligent temperature controller is not limited by the size of the shoe sole 210. As shown in FIG. 10 of the drawings, the intelligent temperature controlling shoe 200 is implemented as a sport shoe. The intelligent temperature controller 1000 is installed in the shoe sole 210.

Figure 11:
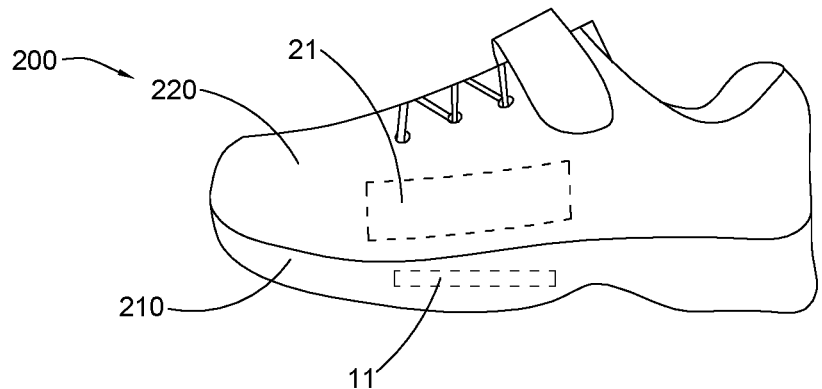
FIG. 11 is a perspective view of the intelligent temperature controlling shoe according to the embodiment of the present invention.

Preferably, as shown in FIG. 11 of the drawings, the intelligent temperature controlling shoe 200 is implemented as a sport shoe, the intelligent temperature controller 1000 is installed both in the shoe sole 210 and the shoe upper 220. Specifically, the heating unit 11 of the intelligent temperature controller 1000 is installed in the shoe sole 210, and the master chip 10, the temperature detecting unit 12, the indicator light 13 and the button 14 are integrated on a circuit board 21. The circuit board 21 is installed in the shoe upper 220. In other embodiment, the power source is also installed in the shoe sole 210.

Figure 12:
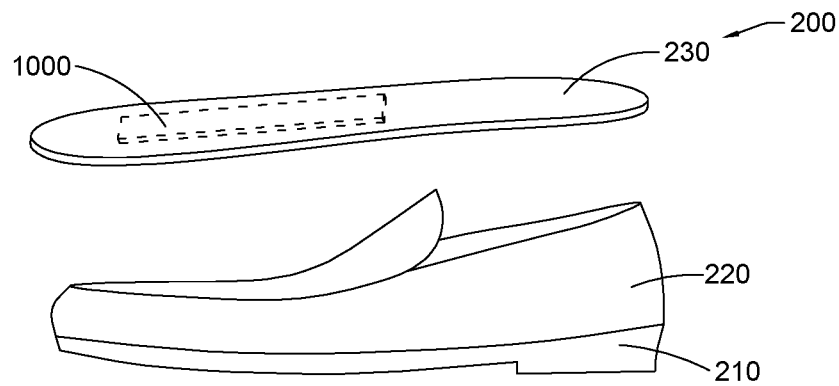
FIG. 12 is a perspective view of the intelligent temperature controlling shoe according to the embodiment of the present invention.

As shown in FIG. 12 of the drawings, the intelligent temperature controlling shoe 200 is implemented as a leather shoe. The intelligent temperature controlling shoe 200 further comprises an insole 230 provided on the shoe sole 210 and inside of the intelligent temperature controlling shoe 200. The intelligent temperature controller 1000 is installed in the insole 230. Therefore, when in use, the insole 230 with the intelligent temperature controller 1000 is put into the intelligent temperature controlling shoe 200 for providing a temperature controlling environment. And after use, the insole with the intelligent temperature controller 1000 can be taken out from the intelligent temperature controlling shoe 200. Accordingly, the insole 230 with the intelligent temperature controller 1000 can be shaped and sized to match various kinds of shoes. In other words, this design enables the user to obtain the intelligent temperature controlling shoe 200 of the present invention by incorporating the insole 230 with the intelligent temperature controller 1000 into a traditional typical shoe without altering the original design of the traditional typical shoe.

As an alternative mode, it is worth mentioning that different parts of the intelligent temperature controller 1000 can be separated and not all of the components are installed in the insole 230. For instance, the heating unit 11 and the power source 15 are placed in the insole 230, and the rest components such as the master chip 10, the temperature detection unit 12, the indication light 13, the button 14, and the charging circuit 16 are installed in the shoe sole 210 or the shoe upper 220. When the insole 230 with the heating unit 11 and the power source 15 is placed into the intelligent temperature controlling shoe 200, the heating unit 11 is connected to the master chip 10, so that the heating unit is under control of the master chip 10 for controlling the temperature.

One skilled in the art will understand that the intelligent temperature controller 1000 is able to be installed in other portions of the intelligent temperature controlling shoe 200, the above mentioned positions and the style of the intelligent temperature controlling shoe 200 is exemplary only and not intended to be limiting.

One skilled in the art will understand that the intelligent temperature controller 1000 being installing in one single intelligent temperature controlling shoe 200 as shown in FIG. 8 to FIG. 12 of the drawings is exemplary only, a pair of the intelligent temperature controlling shoe 200 is able to be respectively installed two intelligent temperature controllers 1000, the amount is not intended to be limiting.

Figure 2:
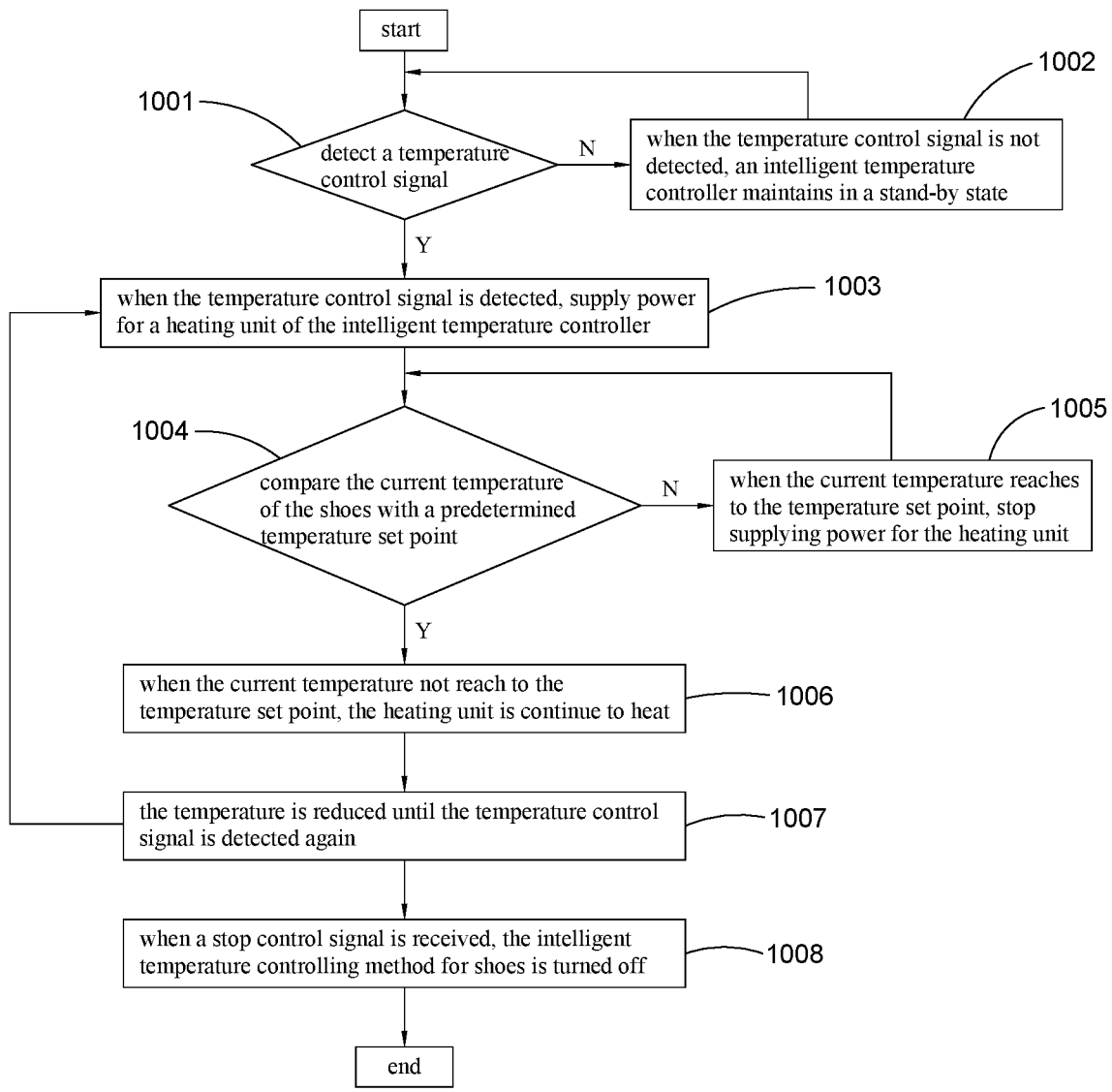
FIG. 2 is a flow diagram of an intelligent temperature controlling method for shoes according to an embodiment of the present invention.

Referring to FIG. 2 of the drawings, an intelligent temperature controlling method for shoes according to the above embodiments of the present invention is illustrated. The intelligent temperature controlling method for shoes comprises the following steps:

(1001) detect a temperature control signal;

(1002) when the temperature control signal is not detected, an intelligent temperature controller maintains in a stand-by state;

(1003) when the temperature control signal is detected, supply power for a heating unit of the intelligent temperature controller;

(1004) compare the current temperature of the shoes with a predetermined temperature set point;

(1005) when the current temperature reaches to the temperature set point, stop supplying power for the heating unit;

(1006) when the current temperature not reach to the temperature set point, the heating unit is continue to heat;

(1007) the temperature is reduced until the temperature control signal is detected again; and (1008) when a stop control signal is received, the intelligent temperature controlling method for shoes is turned off.

Figure 15:
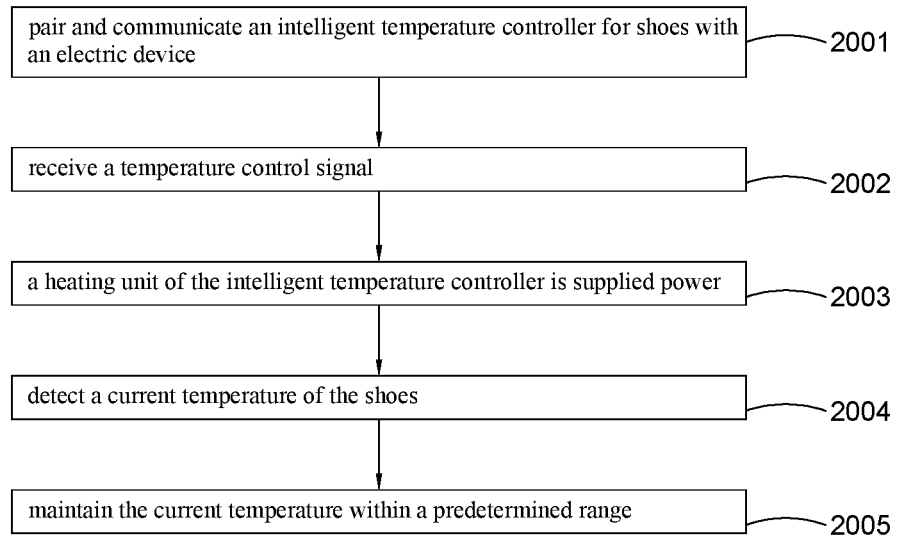
FIG. 15 is a flow diagram of an intelligent temperature controlling method for shoes according to an embodiment of the present invention.

Referring to FIG. 15 of the drawings, an intelligent temperature controlling method for shoes according to the above embodiments of the present invention is illustrated. The intelligent temperature controlling method for shoes comprises the following steps:

(2001) pair and communicate an intelligent temperature controller for shoes with an electric device;

(2002) receive a temperature control signal;

(2003) a heating unit of the intelligent temperature controller is supplied power;

(2004) detect a current temperature of the shoes; and (2005) maintain the current temperature within a predetermined range.

The intelligent temperature controlling method for shoes comprises a step: a Bluetooth device of the intelligent temperature controller for shoes pairs and communicates with the electric device.

The intelligent temperature controlling method for shoes comprises a step: a network wireless transmission device of the intelligent temperature controller for shoes pairs and communicates with the electric device.

The intelligent temperature controlling method for shoes comprises a step: a pulse current generation unit of the intelligent temperature controller for shoes provides pulse current to the heating unit.

The intelligent temperature controlling method for shoes comprises a step: the intelligent temperature controller for shoes feeds back operating state information to the electric device.

The intelligent temperature controlling method for shoes comprises a step: synchronize the time information of the intelligent temperature controller for shoes with the time information of the electric device.

The intelligent temperature controlling method for shoes comprises a step: the intelligent temperature controller for shoes sends warning information to the electric device.

The intelligent temperature controlling method for shoes comprises the following steps:

provide a user account to a user under control of a network service system; and correlate the intelligent temperature controller for shoes with the user account.

The intelligent temperature controlling method for shoes comprises a step: the intelligent temperature controller for shoes is automatically turned on and off in response to an appointment request.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An intelligent temperature controller for a shoe for controlling a temperature of the shoe through a portable electronic device, comprising:

an interactive interface of a software adapted for being installed in the portable electronic device, wherein said interactive interface comprises a time page section, a temperature controlling page section, a warning page section, and an operating state feedback section;

a power source comprising at least a polymer Li-ion battery adapted for being installed in the shoe;

a heating unit, configured for installing to a sole of the shoe, comprising one or more far infrared carbon fiber heating layers such that when said heating unit is supplied with power from said polymer Li-ion battery, said far infrared carbon fiber heating layers generate far infrared wave having a wavelength of 7 to 12 μm;

a master chip, configured for being installed in the shoe, controlling an operative mode of said heating unit, wherein said master chip comprises a Bluetooth device having a unique MAC address for being paired with said interactive interface installed in the portable electronic device to feed back a temperature information to said interactive interface;

a temperature detecting unit electrically connected with said heating unit to automatically control the temperature of the inside of the shoe, wherein said temperature detecting unit detects the temperature of the inside of the shoe, generates detected temperature data and converts said detected temperature data into electrical signal, wherein said electrical signal converted from said detected temperature data is transmitted by said temperature detecting unit to said master chip which controls said operative mode of said heating unit according to said electrical signal transmitted from said temperature detecting unit;

a charging circuit electrically connected to said power source and configured to control a charging of said polymer Li-ion battery of said power source;

a button connected to said master chip, wherein an operating state of said heating unit is controlled by said button; and a circuit board, wherein said master chip, said temperature detecting unit, said button and said charging circuit are integrated on said circuit board to electrically connect to said heating unit, such that said heating unit and said circuit board are located at different locations of the shoe;

wherein said time page section of said interactive interface indicates time setting and display of said intelligent temperature controller, wherein a current time information, including a current time of said intelligent temperature controller, is transmitted by said master chip to be displayed on said time page section of said interactive interface for synchronizing a current time of the portable electronic device with a current time of said intelligent temperature controller;

wherein said temperature controlling page section of said interactive interface indicates a current temperature information including a current temperature of the inside of the shoe detected by said temperature detecting unit, wherein said current temperature information of the inside of the shoe is acquired by said temperature detecting unit and is transmitted by said master chip to said interactive interface and displayed on said temperature controlling page section of said interactive interface, wherein in response to a selecting action of the user of the shoe indicating a temperature rising request on said temperature controlling page section, said master chip receives said temperature rising request and said one or more far infrared carbon fiber heating layers are powered by said polymer Li-ion battery to generate far infrared wave to start heating the inside of the shoe to a desired temperature of the user, wherein in response to a selecting action of the user of the shoe indicating a temperature reducing request on said temperature controlling page section, said master chip receives said temperature reducing request and said polymer Li-ion battery ceases supplying power to said far infrared carbon fiber heating layers to stop heating the shoe, wherein in response to a selecting action of the user indicating a temperature range controlling request on said temperature controlling page section, said master chip acquires said temperature range and said current temperature of the inside of the shoe detected by said temperature detecting unit and controls said one or more far infrared carbon fiber heating layers to selectively heating or stopping to heat when said current temperature of the inside of the shoe detected by said temperature detecting unit is out of said temperature range, so as to control said current temperature of the inside of the shoe within said temperature range;

wherein said feedback page section of said interactive interface indicates operating states of said power unit, said heating unit and said temperature detecting unit of said intelligent temperature controller, wherein said master chip monitors said operating states of said power source, said heating unit and said temperature detecting unit and transmits said operating states to said interactive interface to display on said feedback page section of said interactive interface.

2. The intelligent temperature controller, as recited in claim 1, wherein said interactive interface further comprises a warning page section indicating warning information of said intelligent temperature controller, wherein in response to a set temperature preset by the user of the shoe, said master chip acquires said current temperature detected by said temperature detecting unit that when said current temperature acquired is higher than said set temperature, said master chip sends a temperature warning information to said interactive interface which is displayed on said warning page section for the user to take measure for keeping safety use of the shoe.

3. The intelligent temperature controller, as recited in claim 2, wherein in response to a set electric quantity of the user indicating a charging warning request on said warning page section, said master chip acquires a current electric quantity of said polymer Li-ion battery of said power unit that when said acquired current electric quantity is less than said set electric quantity of the user, said master chip sends a charging warning information to said interactive interface and said charging warning information is displayed on said warning page section.

4. The intelligent temperature controller, as recited in claim 3, wherein said interactive interface further comprises an appointment page section indicating an appointment time of automatically turning on and off of said intelligent temperature controller, wherein in response to a turning on set of the user indicating a set-up request in a predetermined turning on time on said appointment page section, said master chip acquires said current time information, and when a current time is said predetermined turning on time, said master chip controls said one or more far infrared carbon fiber heating layers to start heating the inside of the shoe, wherein in response to a turning off set of the user indicating an off request in a predetermined turning off time, said master chip acquires a current time information, and when said current time is said predetermined turning off time, said master chip performs turning off of said intelligent temperature controller to stop heating by said one or more far infrared carbon fiber heating layers.

5. The intelligent temperature controller, as recited in claim 4, further comprising a pulse current generation unit connected to said master chip to generate a pulse current to power said intelligence temperature controller, such that when the temperature of the shoe reaches a predetermined value, said pulse current is generated to said heating unit for maintaining the temperature of the shoe in a predetermined range.

6. The intelligent temperature controller, as recited in claim 5, wherein said unique MAC address of said Bluetooth device is provided with a unique QR code that enables said Bluetooth device to be paired with said interactive interface of said software installed in the portable electronic device by scanning said unique QR code for said unique MAC address of said Bluetooth device.

7. The intelligent temperature controller, as recited in claim 3, further comprising a pulse current generation unit connected to said master chip to generate a pulse current to power said intelligence temperature controller, such that when the temperature of the shoe reaches a predetermined value, said pulse current is generated to said heating unit for maintaining the temperature of the shoe in a predetermined range.

8. The intelligent temperature controller, as recited in claim 2, wherein said interactive interface further comprises an appointment page section indicating an appointment time of automatically turning on and off of said intelligent temperature controller, wherein in response to a turning on set of the user indicating a set-up request in a predetermined turning on time on said appointment page section, said master chip acquires said current time information, and when a current time is said predetermined turning on time, said master chip controls said one or more far infrared carbon fiber heating layers to start heating the inside of the shoe, wherein in response to a turning off set of the user indicating an off request in a predetermined turning off time, said master chip acquires a current time information, and when said current time is said predetermined turning off time, said master chip performs turning off of said intelligent temperature controller to stop heating by said one or more far infrared carbon fiber heating layers.

9. The intelligent temperature controller, as recited in claim 1, wherein in response to a set electric quantity of the user indicating a charging warning request on said warning page section, said master chip acquires a current electric quantity of said polymer Li-ion battery of said power unit that when said acquired current electric quantity is less than said set electric quantity of the user, said master chip sends a charging warning information to said interactive interface and said charging warning information is displayed on said warning page section.

10. The intelligent temperature controller, as recited in claim 9, further comprising a pulse current generation unit connected to said master chip to generate a pulse current to power said intelligence temperature controller, such that when the temperature of the shoe reaches a predetermined value, said pulse current is generated to said heating unit for maintaining the temperature of the shoe in a predetermined range.

11. The intelligent temperature controller, as recited in claim 9, wherein said unique MAC address of said Bluetooth device is provided with a unique QR code that enables said Bluetooth device to be paired with said interactive interface of said software installed in the portable electronic device by scanning said unique QR code for said unique MAC address of said Bluetooth device.

12. The intelligent temperature controller, as recited in claim 1, wherein said interactive interface further comprises an appointment page section indicating an appointment time of automatically turning on and off of said intelligent temperature controller, wherein in response to a turning on set of the user indicating a set-up request in a predetermined turning on time on said appointment page section, said master chip acquires said current time information, and when a current time is said predetermined turning on time, said master chip controls said one or more far infrared carbon fiber heating layers to start heating the inside of the shoe, wherein in response to a turning off set of the user indicating an off request in a predetermined turning off time, said master chip acquires a current time information, and when said current time is said predetermined turning off time, said master chip performs turning off of said intelligent temperature controller to stop heating by said one or more far infrared carbon fiber heating layers.

13. The intelligent temperature controller, as recited in claim 12, wherein said unique MAC address of said Bluetooth device is provided with a unique QR code that enables said Bluetooth device to be paired with said interactive interface of said software installed in the portable electronic device by scanning said unique QR code for said unique MAC address of said Bluetooth device.

14. The intelligent temperature controller, as recited in claim 1, further comprising a pulse current generation unit connected to said master chip to generate a pulse current to power said intelligence temperature controller, such that when the temperature of the shoe reaches a predetermined value, said pulse current is generated to said heating unit for maintaining the temperature of the shoe in a predetermined range.

15. The intelligent temperature controller, as recited in claim 14, wherein said unique MAC address of said Bluetooth device is provided with a unique QR code that enables said Bluetooth device to be paired with said interactive interface of said software installed in the portable electronic device by scanning said unique QR code for said unique MAC address of said Bluetooth device.

16. The intelligent temperature controller, as recited in claim 1, wherein said unique MAC address of said Bluetooth device is provided with a unique QR code that enables said Bluetooth device to be paired with said interactive interface of said software installed in the portable electronic device by scanning said unique QR code for said unique MAC address of said Bluetooth device.

17. An intelligent temperature controlling method for shoe, comprising the steps of:
controlling an operating state of a heating unit by a button;
charging a power source via a charging circuit;

detecting a current temperature of an inside of a shoe, generating detected temperature data, and converting said detected temperature data into electrical signal by a temperature detecting unit of an intelligent temperature controller installed in the inside of the shoe;

transmitting said electrical signal converted from said detected temperature data to a master chip of said intelligent temperature controller installed in the shoe to control an operative mode of one or more far infrared carbon fiber heating layers of said heating unit of said intelligent temperature controller installed in a sole of the shoe, wherein said master chip, said temperature detecting unit, said button and said charging circuit are integrated on a circuit board to electrically connect to said heating unit, such that said heating unit and said circuit board are located at different locations of the shoe;

comparing said current temperature with a predetermined set temperature;

when said current temperature not reaching said predetermined set temperature, heating the inside of the shoe by said one or more far infrared carbon fiber heating layers of said heating unit controlled by said master chip until said current temperature detected by said temperature detecting unit reaching said predetermined set temperature;

when said current temperature reaching said predetermined set temperature, stopping said one or more far infrared carbon fiber heating layers to heat the inside of the shoe by said master chip;

transmitting a current time information to be display in a time page section of an interactive interface of a software installed in a portable electronic device paired with said master chip, wherein a current time of said intelligent temperature controller is synchronized with a current time of the portable electronic device;

acquiring a current temperature information, including a current temperature of the inside of the shoe, detected by said temperature detecting unit, transmitting by said master chip to said interactive interface, and displaying said current temperature information on a temperature controlling page section of said interactive interface;

in response to a selecting action of the user of the shoe indicating a temperature rising request on said temperature controlling page section, receiving said temperature rising request by said master chip and heating the inside of the shoe by generating far infrared wave having a wavelength of 7 to 12 μm by said one or more far infrared carbon fiber heating layers of said heating unit powered by at least a polymer Li-ion battery of said power source;

in response to a selecting action of the user of the shoe indicating a temperature reducing request on said temperature controlling page section, receiving said temperature reducing request by said master chip and ceasing supply power to said far infrared carbon fiber heating layers of said heating unit to stop heating the shoe;

in response to a selecting action of the user indicating a temperature range controlling request on said temperature controlling page section, acquiring said temperature range and said current temperature of the inside of the shoe detected by said temperature detecting unit and controlling said one or more far infrared carbon fiber heating layers to selectively heating or stopping to heat by said master chip when said current temperature of the inside of the shoe detected by said temperature detecting unit is out of said temperature range, so as to control said current temperature of the inside of the shoe within said temperature range; and monitoring operating states of said power unit, said heating unit and said temperature detecting unit of said intelligent temperature controller, transmitting to said interactive interface and displaying said operating states on a feedback page section of said interactive interface.

18. The intelligent temperature controlling method, as recited in claim 17, further comprising the steps of:

indicating warning information of said intelligence temperature controller on a warning page section of said interactive interface, and in response to a set temperature preset by the user of the shoe, acquiring said current temperature detected by said temperature detecting unit by said master chip that when said current temperature acquired is higher than said set temperature, sending a temperature warning information by said master chip to said interactive interface, and displaying said warning page section for the user to take measure on said warning page section of said interactive interface for keeping safety use of the shoe.

19. The intelligent temperature controlling method, as recited in claim 18, further comprising a step of:

in response to a set electric quantity of the user indicating a charging warning request on a warning page section of said interactive interface, acquiring a current electric quantity of said polymer Li-ion battery of said power unit by said master chip that when said acquired current electric quantity is less than said set electric quantity of the user, sending a charging warning information to said interactive interface and displaying said charging warning information on said warning page section of said interactive interface.

20. The intelligent temperature controlling method, as recited in claim 19, further comprising the steps of:

indicating an appointment time of automatically turning on and off of said intelligent temperature controller on an appointment page section thereof, in response to a turning on set of the user indicating a set-up request in a predetermined turning on time on said appointment page section, acquiring said current time information by said master chip, and when a current time is said predetermined turning on time, controlling said one or more far infrared carbon fiber heating layers to start heating the inside of the shoe by said master chip, and in response to a turning off set of the user indicating an off request in a predetermined turning off time, acquiring a current time information by said master chip, and when said current time is said predetermined turning off time, performing turning off of said intelligent temperature controller by said master chip to stop heating by said one or more far infrared carbon fiber heating layers.

21. The intelligent temperature controlling method, as recited in claim 20, further comprising a step of generating a pulse current by a pulse current generation unit connected to said master chip to power said intelligence temperature controller, such that when the temperature of the shoe reaches a predetermined value, said pulse current is generated to said heating unit for maintaining the temperature of the shoe in a predetermined range.

22. The intelligent temperature controlling method, as recited in claim 21, further comprising a step of scanning a unique QR code identifying a unique MAC address of a Bluetooth device of said master chip to pair said interactive interface of said software installed in the portable electronic device with said Bluetooth device of said master chip.

23. The intelligent temperature controlling method, as recited in claim 20, further comprising a step of scanning a unique QR code identifying a unique MAC address of a Bluetooth device of said master chip to pair said interactive interface of said software installed in the portable electronic device with said Bluetooth device of said master chip.

24. The intelligent temperature controlling method, as recited in claim 18, further comprising a step of generating a pulse current by a pulse current generation unit connected to said master chip to power said intelligence temperature controller, such that when the temperature of the shoe reaches a predetermined value, said pulse current is generated to said heating unit for maintaining the temperature of the shoe in a predetermined range.

25. The intelligent temperature controlling method, as recited in claim 17, further comprising a step of:
in response to a set electric quantity of the user indicating a charging warning request on a warning page section of said interactive interface, acquiring a current electric quantity of said polymer Li-ion battery of said power unit by said master chip that when said acquired current electric quantity is less than said set electric quantity of the user, sending a charging warning information to said interactive interface and displaying said charging warning information on said warning page section of said interactive interface.

26. The intelligent temperature controlling method, as recited in claim 25, further comprising the steps of:
indicating an appointment time of automatically turning on and off of said intelligent temperature controller on an appointment page section thereof,
in response to a turning on set of the user indicating a set-up request in a predetermined turning on time on said appointment page section, acquiring said current time information by said master chip, and when a current time is said predetermined turning on time, controlling said one or more far infrared carbon fiber heating layers to start heating the inside of the shoe by said master chip, and
in response to a turning off set of the user indicating an off request in a predetermined turning off time, acquiring a current time information by said master chip, and when said current time is said predetermined turning off time, performing turning off of said intelligent temperature controller by said master chip to stop heating by said one or more far infrared carbon fiber heating layers.

27. The intelligent temperature controlling method, as recited in claim 25, further comprising a step of generating a pulse current by a pulse current generation unit connected to said master chip to power said intelligence temperature controller, such that when the temperature of the shoe reaches a predetermined value, said pulse current is generated to said heating unit for maintaining the temperature of the shoe in a predetermined range.

28. The intelligent temperature controlling method, as recited in claim 17, further comprising the steps of:
indicating an appointment time of automatically turning on and off of said intelligent temperature controller on an appointment page section thereof,
in response to a turning on set of the user indicating a set-up request in a predetermined turning on time on said appointment page section, acquiring said current time information by said master chip, and when a current time is said predetermined turning on time, controlling said one or more far infrared carbon fiber heating layers to start heating the inside of the shoe by said master chip, and
in response to a turning off set of the user indicating an off request in a predetermined turning off time, acquiring a current time information by said master chip, and when said current time is said predetermined turning off time, performing turning off of said intelligent temperature controller by said master chip to stop heating by said one or more far infrared carbon fiber heating layers.

29. The intelligent temperature controlling method, as recited in claim 28, further comprising a step of generating a pulse current by a pulse current generation unit connected to said master chip to power said intelligence temperature controller, such that when the temperature of the shoe reaches a predetermined value, said pulse current is generated to said heating unit for maintaining the temperature of the shoe in a predetermined range.

30. The intelligent temperature controlling method, as recited in claim 17, further comprising a step of generating a pulse current by a pulse current generation unit connected to said master chip to power said intelligence temperature controller, such that when the temperature of the shoe reaches a predetermined value, said pulse current is generated to said heating unit for maintaining the temperature of the shoe in a predetermined range.

31. The intelligent temperature controlling method, as recited in claim 17, further comprising a step of scanning a unique QR code identifying a unique MAC address of a Bluetooth device of said master chip to pair said interactive interface of said software installed in the portable electronic device with said Bluetooth device of said master chip.

\* \* \* \* \*